(12) United States Patent
Ushio

(10) Patent No.: US 10,859,811 B2
(45) Date of Patent: Dec. 8, 2020

(54) RELAY OPTICAL SYSTEM AND RIGID ENDOSCOPE USING THE SAME

(71) Applicant: OLYMPUS CORPORATION, Hachioji (JP)

(72) Inventor: Yasuaki Ushio, Halstenbek (DE)

(73) Assignee: OLYMPUS CORPORATION, Tokyo (JP)

( * ) Notice: Subject to any disclaimer, the term of this patent is extended or adjusted under 35 U.S.C. 154(b) by 225 days.

(21) Appl. No.: 16/125,635

(22) Filed: Sep. 7, 2018

(65) Prior Publication Data

US 2019/0004307 A1 Jan. 3, 2019

Related U.S. Application Data

(63) Continuation of application No. PCT/JP2017/014121, filed on Apr. 4, 2017.

(30) Foreign Application Priority Data

May 20, 2016 (JP) ................................ 2016-101270

(51) Int. Cl.
*G02B 23/24* (2006.01)
*G02B 13/18* (2006.01)
(Continued)

(52) U.S. Cl.
CPC .......... *G02B 23/2446* (2013.01); *A61B 1/002* (2013.01); *A61B 1/00078* (2013.01);
(Continued)

(58) Field of Classification Search
CPC ............... G02B 23/24; G02B 23/2446; G02B 13/0095; G02B 13/18; A61B 1/0005;
(Continued)

(56) References Cited

U.S. PATENT DOCUMENTS 3,799,656 A * 3/1974 Fleischman ............ G02B 13/00
359/777
4,545,652 A 10/1985 Hoogland
(Continued)

FOREIGN PATENT DOCUMENTS

JP S57207215 A 12/1982
JP 61184513 A 6/1986
(Continued)

OTHER PUBLICATIONS

International Search Report (ISR) dated Jul. 4, 2017 issued in International Application No. PCT/JP2017/014121.
(Continued)

*Primary Examiner* — Thong Q Nguyen
(74) *Attorney, Agent, or Firm* — Holtz, Holtz & Volek PC

(57) ABSTRACT

A relay optical system includes, in order from, an object side, a first cemented lens, a second cemented lens having a positive refractive power, a third cemented lens which is plane-symmetric to the second cemented lens, and a fourth cemented lens which is plane-symmetric to the first cemented lens, the first cemented lens includes a first lens having a positive refractive power and a second lens having a negative refractive power, the second cemented lens includes a third lens and a fourth lens, a shape of the first lens is a biconvex shape, a shape of the second lens is a biconcave shape, and the following conditional expression (1), in which f2 denotes a focal length of the second lens and fCL12 denotes a combined focal length of the first cemented lens and the second cemented lens, is satisfied:

$$-0.4 < f2/fCL12 < -0.1 \qquad (1).$$

8 Claims, 12 Drawing Sheets

(51) Int. Cl.
*G02B 23/26* (2006.01)
*G02B 13/00* (2006.01)
*A61B 1/002* (2006.01)
*A61B 1/00* (2006.01)
*G02B 9/60* (2006.01)

(52) U.S. Cl.
CPC ...... *A61B 1/00188* (2013.01); *A61B 1/00195* (2013.01); *G02B 9/60* (2013.01); *G02B 13/00* (2013.01); *G02B 13/18* (2013.01); *G02B 23/26* (2013.01)

(58) Field of Classification Search
CPC ............ A61B 1/00096; A61B 1/00163; A61B 1/00188; A61B 1/002
See application file for complete search history.

(56) References Cited

U.S. PATENT DOCUMENTS

| | | |
|---|---|---|
| 4,575,195 A | 3/1986 | Hoogland |
| 4,676,606 A | 6/1987 | Takahashi |
| 4,693,568 A * | 9/1987 | Takahashi ................ G02B 9/34 359/772 |
| 5,461,509 A * | 10/1995 | Canzek .................. A61B 1/042 359/362 |
| 5,743,846 A * | 4/1998 | Takahashi .......... A61B 1/00193 600/111 |
| 2008/0239480 A1 | 10/2008 | Tomioka |

FOREIGN PATENT DOCUMENTS

| | | |
|---|---|---|
| JP | 2000010024 A | 1/2000 |
| JP | 2007522507 A | 8/2007 |
| JP | 2015118136 A | 6/2015 |
| JP | 6029159 B1 | 11/2016 |

OTHER PUBLICATIONS

International Preliminary Report on Patentability (IPRP) (and English translation thereof) dated Nov. 20, 2018 in counterpart International Application PCT/JP2017/014121.

* cited by examiner

FIG. 2A
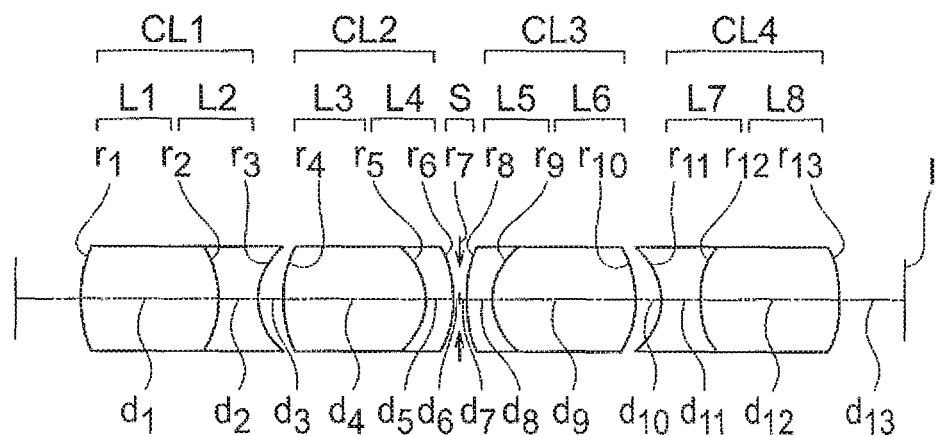
FIG. 2B
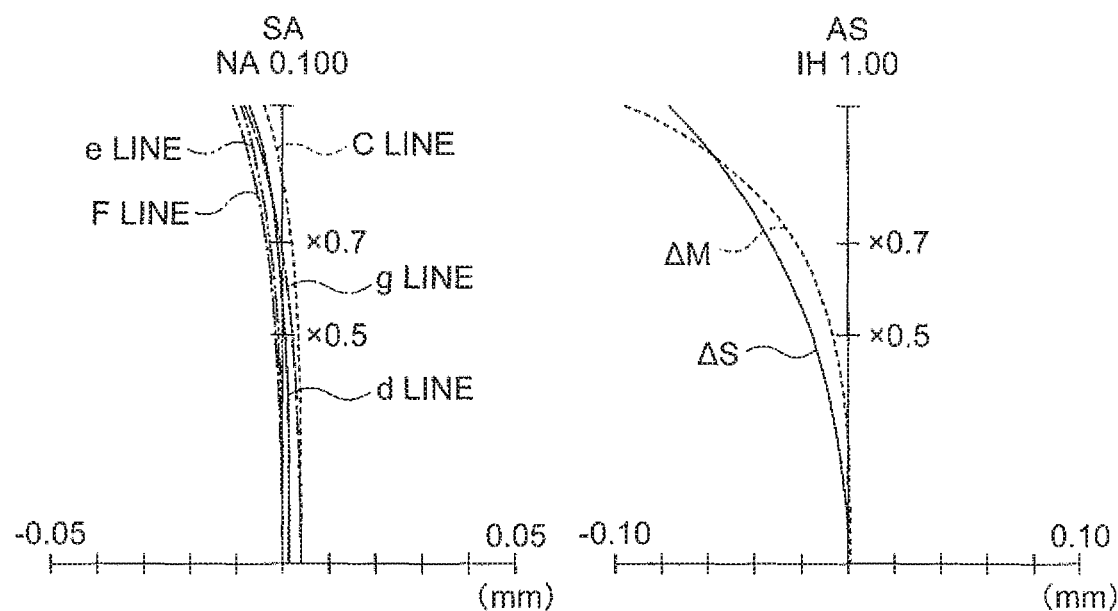
FIG. 2C

FIG. 3A
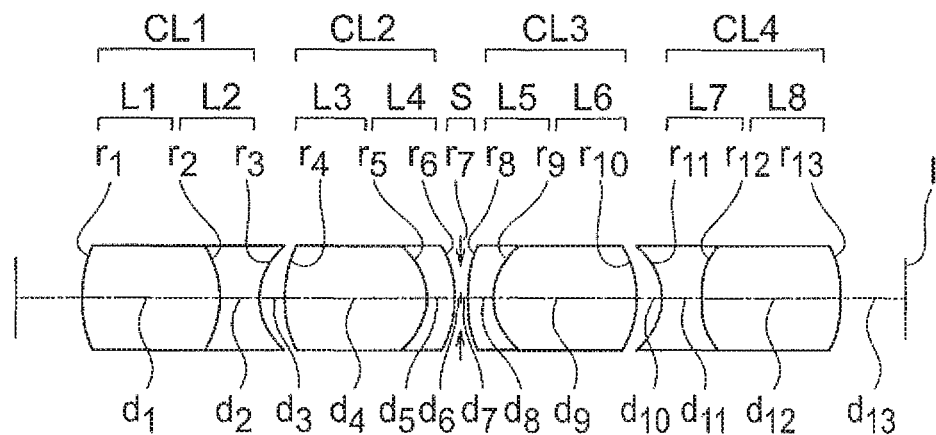
FIG. 3B
FIG. 3C
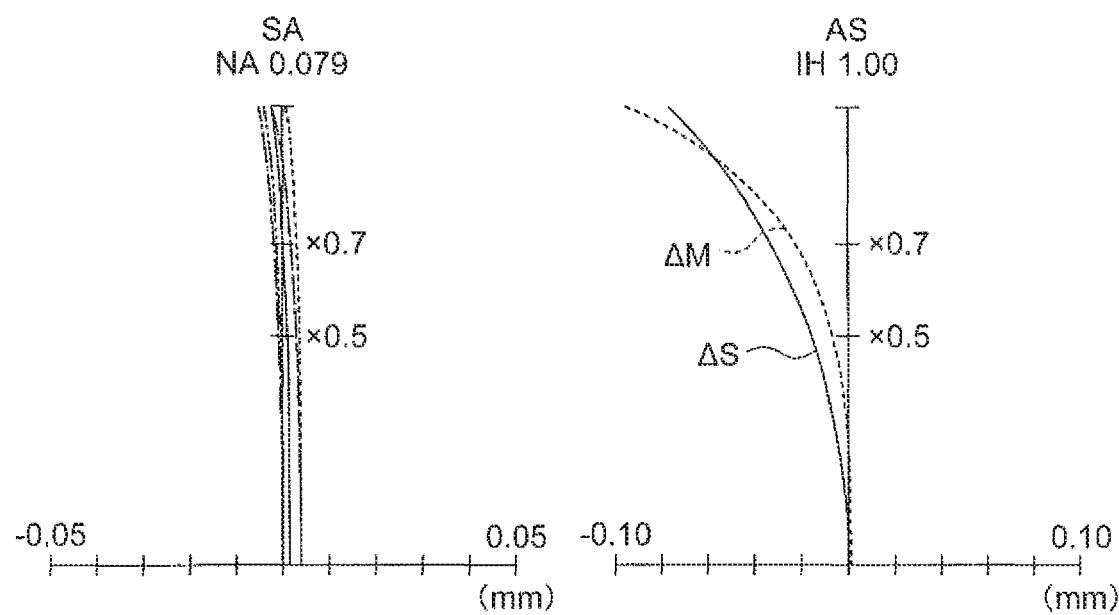

FIG. 9A
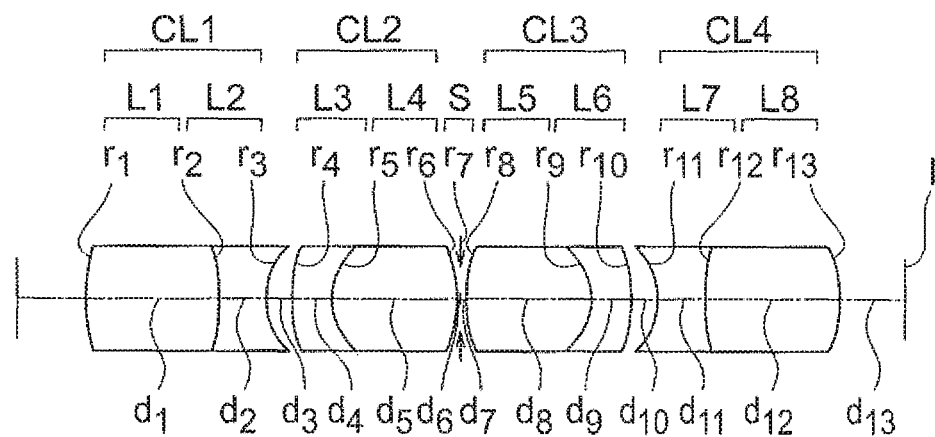
FIG. 9B
FIG. 9C
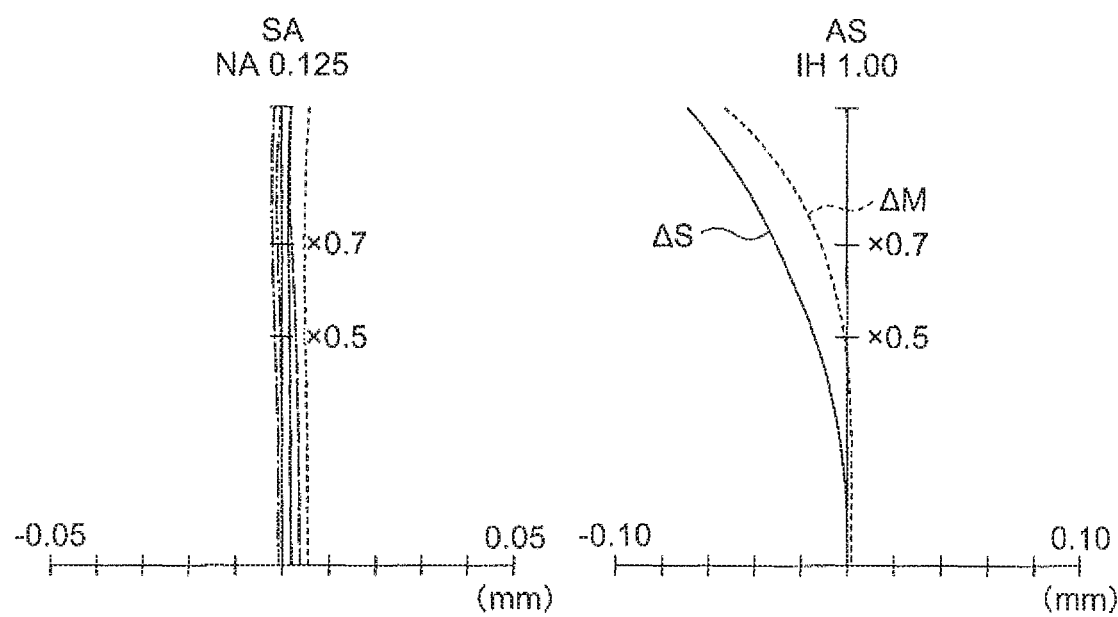

FIG. 11A
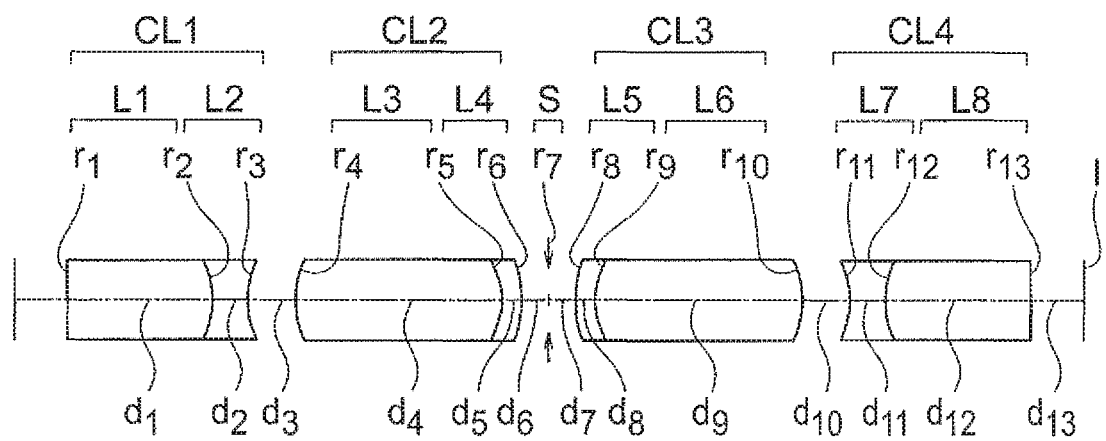
FIG. 11B
FIG. 11C
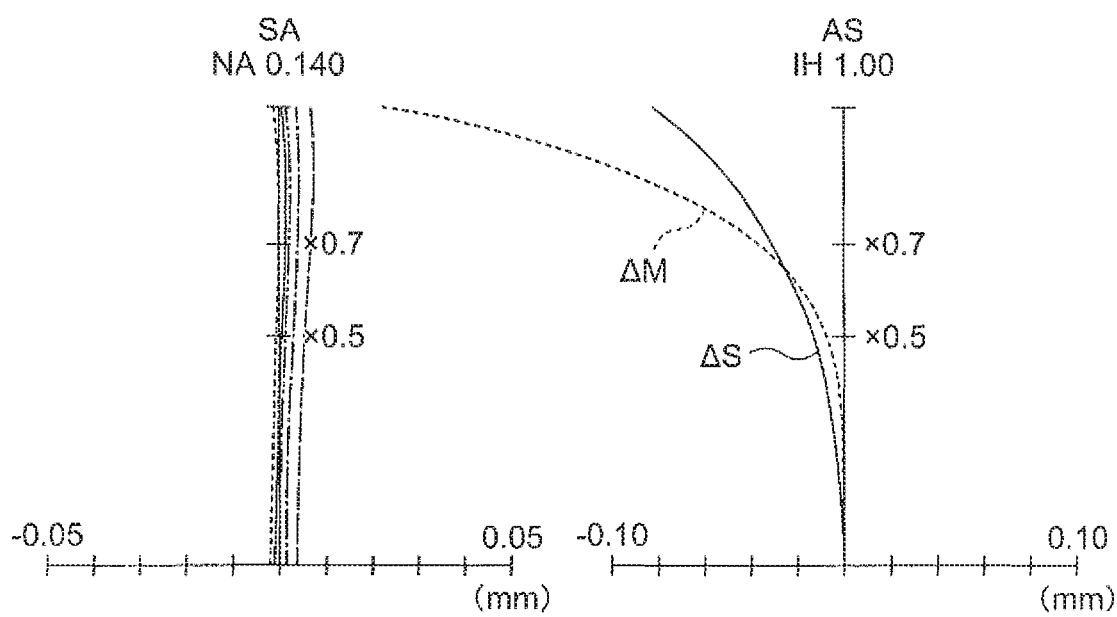

RELAY OPTICAL SYSTEM AND RIGID ENDOSCOPE USING THE SAME

CROSS-REFERENCE TO RELATED APPLICATION

The present application is a continuation application of PCT/JP2017/014121 filed on Apr. 4, 2017 which is based upon and claims the benefit of priority from Japanese Patent Application No. 2016-101270 filed on May 20, 2016; the entire contents of which are incorporated herein by reference.

BACKGROUND OF THE INVENTION

Field of the Invention

The present invention relates to a relay optical system and a rigid endoscope using the same.

Description of the Related Art

In recent years, in diagnosis using a rigid endoscope, an improvement in accuracy of diagnosis has been desired. In order to meet with this requirement, rigid endoscopes are expected to enable observation an object with a high resolution and acquisition of an image of an object with a high image quality.

The observation of the object and the acquisition of the image of the object is achieved via an observation optical system disposed inside a rigid endoscope. In the acquisition of the image of the object, a camera head is to be connected to the observation optical system. In the camera head, a CCD (Charge Coupled Device) or a C-MOS (Complementary Metal Oxide Semiconductor) is used as an image pickup element.

The observation optical system includes an objective lens, an eyepiece, and a plurality of relay optical systems. The plurality of relay optical systems is disposed between the objective lens and the eyepiece.

An image (hereinafter, referred to as 'primary image') of an object is formed by the objective lens. The primary image becomes an inverted image or in other words, an image in which the object is inverted in a vertical direction. In the relay optical system, the primary image is relayed. An image formed by the relay optical system is also an inverted image. The primary image is an inverted image and the image relayed is also an inverted image. Therefore, an image that is relayed once becomes an erect image. In a rigid endoscope, usually, an erect image is to be observed or captured. The primary image being the inverted image, the number of relay optical systems becomes odd.

In Japanese Unexamined Patent Application Publication No. 2007-522507, Japanese Patent Application Laid-open Publication No. 2000-010024, and Japanese Patent Application Laid-open Publication No. 2015-118136, relay optical systems have been disclosed.

SUMMARY OF THE INVENTION

A relay optical system according to at least some embodiments of the present invention comprises in order from an object side,
  a first cemented lens,
  a second cemented lens having a positive refractive power,
  a third cemented lens which is plane-symmetric to the second cemented lens, and
  a fourth cemented lens which is plane-symmetric to the first cemented lens, wherein
  the first cemented lens includes a first lens having a positive refractive power and second lens having a negative refractive power, and
  the second cemented lens includes a third lens and a fourth lens, and
  a shape of the first lens is a biconvex shape, and
  a shape of the second lens is a biconcave shape, and
  the following conditional expression (1) is satisfied:

$$-0.4 < f2/fCL12 < -0.1 \tag{1}$$

where,
f2 denotes a focal length of the second lens, and
fCL12 denotes a combined focal length of the first cemented lens and the second cemented lens.

Moreover, a rigid endoscope of the present invention comprises the abovementioned relay optical system.

BRIEF DESCRIPTION OF THE DRAWINGS

FIG. 2A, and FIG. 2B and FIG. 2C, are a lens cross-sectional view and aberration diagrams respectively, of a relay optical system according to an example 1;

FIG. 3A, and FIG. 3B and FIG. 3C, are a lens cross-sectional view and aberration diagrams respectively, of a relay optical system according to an example 2;

FIG. 9A, and FIG. 9B and FIG. 9C, are a lens cross-sectional view and aberration diagrams respectively, of a relay optical system according to an example 8;

FIG. 11A, and FIG. 11B and FIG. 11C, are a lens cross-sectional view and aberration diagrams respectively, of a relay optical system according to an example 10.

DETAILED DESCRIPTION OF THE INVENTION

Reasons for and an effect of adopting such arrangements for a relay optical system according to the present embodiment will be described below by using the accompanying diagrams. However, the present invention is not restricted to the embodiment described below.

A relay optical system is used for relaying an image. An image to be relayed by the relay optical system is formed by an objective lens for example. The objective lens is disposed between an object and the relay optical system. A primary image is formed by the objective lens. The relay optical system forms an image by relaying the primary image. An object side in the following description refers to a primary-image side.

The relay optical system of the present embodiment includes in order from an object side, a first cemented lens, a second cemented lens having a positive refractive power, a third cemented lens which is plane-symmetric to the second cemented lens, and a fourth cemented lens which is plane-symmetric to the first cemented lens. The first cemented lens includes a first lens having a positive refractive power and a second lens having a negative refractive power. The second cemented lens includes a third lens and a fourth lens. A shape of the first lens is a biconvex shape and a shape of the second lens is a biconcave shape, and the following conditional expression (1) is satisfied:

$$-0.4 < f2/fCL12 < -0.1 \quad (1)$$

where, f2 denotes a focal length of the second lens, and fCL12 denotes a combined focal length of the first cemented lens and the second cemented lens.

Figure 1A:
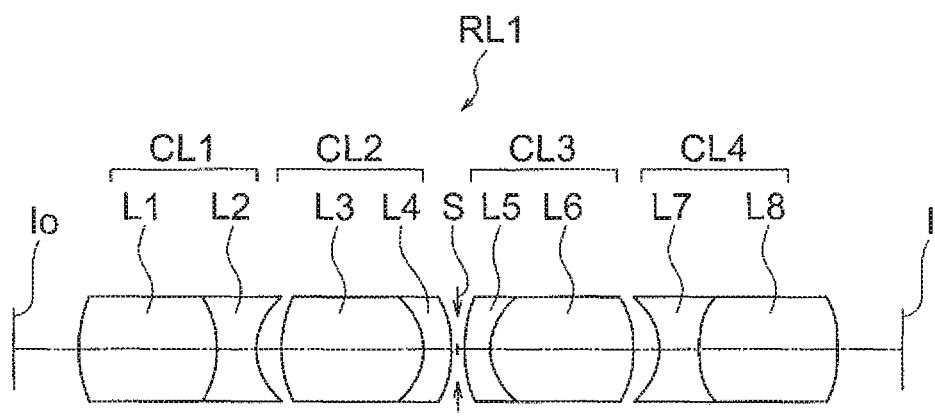
FIG. 1A and FIG. 1B are lens cross-sectional views showing a basic arrangement of a relay optical system according to the present embodiment.
Figure 1B:
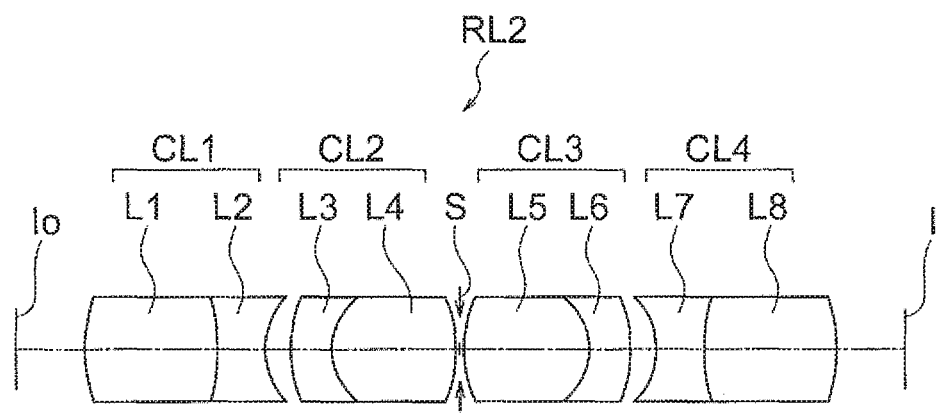

FIG. 1A and FIG. 1B show a basic arrangement of the relay optical system of the present embodiment. FIG. 1A is a lens cross-sectional view of an arrangement example 1 and FIG. 1B is a cross-sectional view of an arrangement example 2. The arrangement example 1 and the arrangement example 2 have many points in common. Therefore, in the following description, the description will be made by using the arrangement example 1, and points of the arrangement example 2 differing from the arrangement example 1 will be described.

In the arrangement example 1, a relay optical system RL1 includes a first cemented lens CL1, a second cemented lens CL2, a third cemented lens CL3, and a fourth cemented lens CL4. An aperture stop S is disposed between the second cemented lens CL2 and the third cemented lens CL3.

In FIG. 1A and FIG. 1B, a leftward direction on a paper surface is let to be an object side and a rightward direction on the paper surface is let to be an image side. An objective lens (not shown in the diagram) is disposed on the object side of the relay optical system RL1. A primary image Io is formed by the objective lens. In the relay optical system RL1, the primary image Io is relayed. As a result, a relayed image I is formed on the image side of the relay optical system RL1.

In the relay optical system RL1, two sets of cemented lenses are disposed to be plane-symmetric. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second cemented lens CL2.

In the relay optical system RL1, the first cemented lens CL1 and the fourth cemented lens CL4 are symmetrical with respect to the aperture stop S. Moreover, the second cemented lens CL2 and the third cemented lens CL3 are symmetrical with respect to the aperture stop S. In the relay optical system RL1, a plane of symmetry is at a position of the aperture stop S.

In such manner, the relay optical system RL1 has a plurality of sets of cemented lenses that are plane-symmetric, in the optical system. Therefore, it is possible to correct a coma aberration and a chromatic aberration of magnification favorably.

The first cemented lens CL1 includes a first lens L1 and a second lens L2. The first lens L1 has a positive refractive power and the second lens L2 has a negative refractive power. Accordingly, in the first cemented lens, it is possible to correct mainly a curvature of field favorably.

The second cemented lens CL2 includes a third lens L3 and a fourth lens L4. In the relay optical system RL1, the third lens L3 has a positive refractive power, and the fourth lens L4 has a negative refractive power. In a relay optical system RL2, a third lens L3 has a negative refractive power and a fourth lens L4 has a positive refractive power.

At a position of the second cemented lens CL2, a height of an axial light ray becomes higher as compared to a height at a position of the first cemented lens CL1. By the second cemented lens CL2 having two lenses, it is possible to correct the chromatic aberration and the spherical aberration favorably.

The shape of the first lens L1 is a biconvex shape. Therefore, a light ray incident on the first lens L1 is refracted toward an optical axial direction. Accordingly, it is possible to make small a diameter of a light beam that is incident. As a result, it is possible to make an effective aperture of the lens small.

The shape of the second lens L2 is a biconcave shape. By making such arrangement, it is possible to correct favorably the curvature of field and the spherical aberration.

When the shape of the second lens L2 is let to be a biconcave shape, it is possible to impart easily a large negative refractive power to the second lens L2. When it is possible to make the negative refractive power of the second lens L2 large, it is possible to make Petzval sum for the overall relay optical system small. As a result, it is possible to correct favorably the curvature of field in particular.

In the arrangement example 1 and the arrangement example 2, the aperture stop S is disposed in the relay optical system. A metallic plate provided with an opening for example, is used as the aperture stop S. A light-beam diameter is determined by a size of the opening. The aperture stop S is not required to be disposed in the relay optical system, provided that it is possible to determine the light-beam diameter even without using the aperture stop S.

The relay optical system of the present embodiment includes either the arrangement example 1 or the arrangement example 2, and the abovementioned conditional expression (1) is satisfied.

By satisfying conditional expression (1), it is possible to impart an appropriate large negative refractive power to the second lens. As a result, it is possible to correct favorably the chromatic aberration and the spherical aberration while correcting favorably the curvature of field.

In a case of falling below a lower limit value of conditional expression (1), the negative refractive power of the second lens becomes small. In this case, since the curvature of field increases, imaging performance at periphery of an image is degraded. In a case of exceeding an upper limit value of conditional expression (1), the negative refractive power of the second lens becomes large. In this case, since the chromatic aberration and the spherical aberration increase, it is not possible to achieve a favorable imaging performance over a wide range from a center up to a periphery of the image.

When the numerical aperture of the optical system is made large, an amount of aberration that occurs is susceptible to increase. The relay optical system of the present embodiment is an optical system with high capability of correcting various aberrations. Therefore, in the relay optical system of the present embodiment, even when the numerical aperture is made large, it is possible to suppress as increase in the curvature of field, an increase in the spherical aberration, and an increase in the chromatic aberration. In such manner, according to the relay optical system of the present embodiment, it is possible to realize a relay optical system having a large numerical aperture and a high imaging performance.

It is preferable that the following conditional expression (1') or (1") be satisfied instead of conditional expression (1).

$$-0.4 < f2/fCL12 < -0.13 \quad (1')$$

$$-0.38 < f2/fCL12 < -0.15 \quad (1'')$$

In the relay optical system of the present embodiment, it is preferable that the third lens have a positive refractive power, and the fourth lens have a negative refractive power, or the third lens have a negative refractive power and the fourth lens have a positive refractive power.

By making such arrangement, it is possible to correct the chromatic aberration at a position at which a height of an axial image ray becomes even higher. Consequently, it is possible to correct the chromatic aberration more favorably.

In the relay optical system of the present embodiment, it is preferable that a lens surface on the object side of the third lens be an aspheric surface.

By making such arrangement, it is possible to correct the spherical aberration more favorably. In other words, it is possible to maintain a high imaging performance even when the numerical aperture is made large. As a result, it is possible to form an image with a high resolution.

In the relay optical system of the present embodiment, it is preferable that the following conditional expression (2) be satisfied:

$$3 < PS \times TL < 8 \quad (2)$$

where,
PS denotes Petzval sum, and
TL denotes an overall length of the relay optical system.

In the relay optical system, the refractive power of the overall system is a positive refractive power. The relay optical system includes the positive lens and the negative lens. Therefore, the refractive power of the overall relay optical system is determined by a magnitude of the refractive power of the positive lens and a magnitude of the refractive power of the negative lens.

By satisfying conditional expression (2), it is possible to make large a proportion of the negative refractive power in the refractive power of the overall relay optical system. As a result, it is possible to correct the curvature of field favorably.

In a case of exceeding an upper limit value of conditional expression (2), the proportion of the negative refractive power in the refractive power of the overall relay optical system becomes small. Consequently, it is not possible to correct the curvature of field adequately. In a case of falling below a lower limit value of conditional expression (2), it is not possible to correct the spherical aberration favorably.

It is preferable that the following conditional expression (2') or (2") be satisfied instead of conditional expression (2).

$$3.5 < PS \times TL < 7.5 \quad (2')$$

$$3.5 < PS \times TL < 7 \quad (2'')$$

In the relay optical system of the present embodiment, it is preferable that the following conditional expression (3) be satisfied:

$$0.5E-5 < |(fCL2/fCL1) \times (\theta gF3 - \theta gF4)/(vd3-vd4)| < 100E-5 \quad (3)$$

where,
fCL1 denotes a focal length of the first cemented lens,
fCL2 denotes a focal length of the second cemented lens,
θgF3 denotes a partial dispersion ratio for the third lens,
θgF4 denotes a partial dispersion ratio for the fourth lens,
vd3 denotes Abbe's number for the third lens, and
vd4 denotes Abbe's number for the fourth lens.

Here, (fCL2×(θgF3−θgF4)/(vd3−vd4) indicates a secondary spectrum of the second cemented lens, or more specifically, an amount of residual aberration for a g-line with respect to an F-line. Moreover, 'E−5' indicates '$10^{-5}$'.

By satisfying conditional expression (3), it is possible to correct the secondary spectrum favorably. As a result, it is possible to form an image with a high resolution.

In a rigid endoscope, an image is relayed for a plurality of times by a plurality of relay optical systems. In this case, an amount of the second spectrum that occurs finally is an amount obtained by multiplying an amount of secondary spectrum in one relay optical system by the number of relays. Therefore, it is preferable to make the amount of secondary spectrum in one relay optical system as small as possible.

As mentioned above, in the relay optical system of the present embodiment, the secondary spectrum has been corrected favorably. Therefore, even the relay optical system of the present embodiment is used for an optical system of a rigid endoscope it is possible to make small the amount of secondary spectrum that occurs finally. As a result, it is possible to form an image with a high resolution.

In a case of exceeding an upper limit value of conditional expression (3), since the secondary spectrum becomes large, it becomes difficult to form an image with a high resolution. In a case of falling below a lower limit value of conditional expression (3), it is not possible to correct the spherical aberration favorably.

It is preferable that the following conditional expression (3') or (3") be satisfied instead of conditional expression (3).

$$1E-5 < |(fCL2/fCL1) \times (\theta gF3 - \theta gF4)/(vd3-vd4)| < 80E-5 \quad (3')$$

$$1E-5 < |(fCL2/fCL1) \times (\theta gF3 - \theta gF4)/(vd3-vd4)| < 30E-5 \quad (3'')$$

In the relay optical system of the present embodiment, it is preferable that the following conditional expression (4) be satisfied:

$$-0.5 < f2/fCL2 < -0.2 \quad (4)$$

where,
f2 denotes the focal length of the second lens, and
fCL2 denotes the focal length of the second cemented lens.

By satisfying conditional expression (4), it is possible to make large a proportion of the negative refractive power in the refractive power of the overall relay optical system. As a result, it is possible to correct the chromatic aberration and the spherical aberration favorably while correcting the curvature of field favorably.

In a case of falling below a lower limit value of conditional expression (4), the proportion of the negative refractive power in the refractive power of the overall relay optical system becomes small. In this case, since the curvature of field is deteriorated, it leads to degradation of imaging performance in a peripheral portion of an image. In a case of exceeding an upper limit value of conditional expression (4), the spherical aberration and the chromatic aberration are deteriorated. Consequently, it becomes difficult to form an image with a high resolution.

It is preferable that the following conditional expression (4') or (4") be satisfied instead of conditional expression (4).

$$-0.5 < f2/fCL2 < -0.23 \quad (4')$$

$$-0.47 < f2/fCL2 < -0.26 \quad (4'')$$

In the relay optical system of the present embodiment, it is preferable that the following conditional expression (5) be satisfied:

$$0.25 < f1/fCL12 < 1 \quad (5)$$

where, f1 denotes a focal length of the first lens, and fCL12 denotes the combined focal length of the first cemented lens and the second cemented lens.

By satisfying conditional expression (5), it is possible to make the positive refractive power of the first lens of an appropriate magnitude. Accordingly, it is also possible to make the negative refractive power of the second lens of an appropriate magnitude. As a result, it is possible to correct the chromatic aberration and the spherical aberration favorably while correcting the curvature of field favorably.

It is preferable that the following conditional expression (5') or (5") be satisfied instead of conditional expression (5).

$$0.28 < f1/fCL12 < 0.7 \quad (5')$$

$$0.3 < f1/fCL12 < 0.5 \quad (5'')$$

In the relay optical system of the present embodiment, it is preferable that the following conditional expression (6) be satisfied:

$$0.07 < NA \quad (6)$$

where,

NA denotes a numerical aperture of the relay optical system.

By satisfying conditional expression (6), it is possible to form a bright image with a high resolution.

It is preferable that the following conditional expression (6') or (6") be satisfied instead of conditional expression (6).

$$0.09 < NA \quad (6')$$

$$0.105 < NA \quad (6'')$$

A rigid endoscope of the present embodiment includes a relay optical system according to present embodiment.

The rigid endoscope of the present embodiment includes a plurality of relay optical systems. Moreover, in the rigid endoscope of the present embodiment, the relay optical system according to the present embodiment is used at least for one of the plurality of relay optical systems. In the relay optical system of the present embodiment, since Petzval sum becomes small, it is possible to make the curvature of field small. Consequently, by using at least one relay optical system of the present embodiment, it is possible to form an image with a high resolution.

In such manner, according to the rigid endoscope of the present embodiment, it is possible to acquire an image with a high resolution. Moreover, by capturing an image with a high resolution, it is possible to acquire an image of a high image quality.

It is preferable that the rigid endoscope of the present embodiment includes an objective lens, an eyepiece, and a relay optical system which is disposed between the objective lens and the eyepiece, and the total number of relay optical systems is not less than seven, and the total number of relay optical systems of the present embodiment is not less than three.

In the relay optical system of the present embodiment, since Petzval sum becomes small, it is possible to make the curvature of field small. Therefore, in a case in which the total number of relay optical systems is seven or more than seven, by letting the total number of relay optical systems of the present embodiment to be three or more than three, it is possible to form an image with a high resolution. As a result, according to the rigid endoscope of the present embodiment, it is possible to acquire an image with a high resolution. Moreover, by capturing an image with a high resolution, it is possible to achieve an image of a high image quality.

Let us assume that a rigid-endoscope optical system includes an objective lens, an eyepiece, and a plurality of relay optical systems. In this case, it is desirable that in each of the objective lens, the eyepiece, and the relay optical systems, a numerical aperture of an image side is same as or larger than a numerical aperture of the relay optical system of the present embodiment.

By making such arrangement, since the aberration is corrected favorably, it is possible to form a bright image with a high resolution. Moreover, by capturing an image with a high resolution, it is possible to acquire an image of a high image quality.

Figure 12:
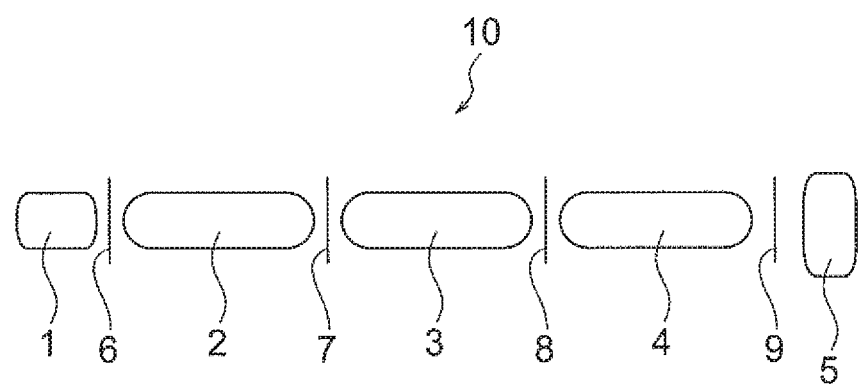
FIG. 12 is a diagram showing a rigid endoscope.

FIG. 12 is a diagram showing a rigid endoscope. In FIG. 12, an observation optical system of the endoscope is shown schematically. Therefore, optical elements in the observation optical system are shown by single lenses.

An observation optical system 10 is disposed at an interior of a rigid tube. The observation optical system 10 includes in order from an object side, an objective lens 1, a relay optical system 2, a relay optical system 3, a relay optical system 4, and an eyepiece 5.

The objective lens 1 forms a primary image on an image plane 6. The primary image is relayed to an image side by the relay optical system 2. Accordingly, a first relay image is formed on an image plane 7. The first relay image is relayed to an image side by the relay optical system 3. Accordingly, a second relay image is formed on an image plane 8. The second relay image is relayed to an image side by the relay optical system 4. Accordingly, a third relay image is formed on an image plane 9.

It is possible to observe the third relay image by the eyepiece 5. A camera-head optical system including an image pickup element may be disposed on the image side (right side) of the eyepiece 5. By making such arrangement, it is possible to acquire an image of an object.

The number of relay optical systems in the observation optical system shown in FIG. 12 is three. However, the number of relay optical systems is not restricted to three. It is possible to make the total number of relay optical systems seven or more than seven for example.

As the total number of relay optical systems is increased, an overall length of the rigid tube becomes long. As the total length of the rigid tube becomes long, operability is degraded. For such reason, the overall length of the rigid tube becomes restricted. For increasing the total number of relay optical systems in the restricted length, an overall length of one relay optical system is to be made short. This signifies that a focal length of one relay optical system becomes short.

When the focal length becomes short without a value of an effective aperture being unchanged, the numerical aperture becomes large. Therefore, when the focal length of the relay optical system becomes short, the numerical aperture of the relay optical system becomes large.

As mentioned above, when the numerical aperture of the optical system is made large, an amount of aberration that occurs is susceptible to increase. However, the relay optical system of the present embodiment is an optical system having a high capability of correcting various aberrations. Therefore, in the relay optical system of the present embodiment, even when the numerical aperture is made large, it is possible to suppress an increase in various aberrations. In other words, even when the total number of relay optical systems is increased, it is possible to maintain a high imaging performance and to form a bright image.

In case of making the total number of relay optical systems seven or more than seven, by making the total number of relay optical systems of the present embodiment three or more than three, it is possible to suppress an increase in the curvature of field, an increase in the spherical aberration, and an increase in the chromatic aberration.

Therefore, according to the rigid endoscope of the present embodiment, it is possible to acquire an image with a high resolution. Moreover, by capturing an image with a high resolution, it is possible to acquire an image of a high image quality.

Examples will be described below. In each aberration diagram, a horizontal axis indicates an amount of aberration. The unit for the spherical aberration and an astigmatism is mm. Moreover, NA denotes the numerical aperture and IH denotes an image height. The unit for a wavelength of an aberration curve is nm.

In each embodiment, an aperture stop S is disposed in a relay optical system. However, the aperture stop S may not be disposed in the relay optical system, provided that it is possible to determine a light-beam diameter without using the aperture stop S.

EXAMPLE 1

A relay optical system according to an example 1 will be described below. FIG. 2A is a lens cross-sectional view of the relay optical system according to the example 1. Moreover, FIG. 2B and FIG. 2C are aberration diagrams of the relay optical system according to the example 1, where, FIG. 2B shows a spherical aberration (SA) and FIG. 2C shows an astigmatism (AS).

The relay optical system of the example 1 includes in order from an object side, a first cemented lens CL1 having a positive refractive power, a second cemented lens CL2 having a positive refractive power, a third cemented lens CL3 having a positive refractive power, and a fourth cemented lens CL4 having a positive refractive power. An aperture stop S is disposed between the second cemented lens CL2 and the third cemented lens CL3.

The first cemented lens CL1 includes a biconvex positive lens L1 and a biconcave negative lens L2. The second cemented lens CL2 includes a biconvex positive lens L3 and a negative meniscus lens L4 having a convex surface directed toward an image side. The third cemented lens CL3 includes a negative meniscus lens L5 having a convex surface directed toward the object side and a biconvex positive lens L6. The fourth cemented lens CL4 includes a biconcave negative lens L7 and a biconvex positive lens L8.

In the relay optical system of the example 1, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at position plane-symmetric to the second cemented lens CL2.

In the relay optical system of the example 1, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 1, a plane of symmetry is at a position of the aperture stop S.

EXAMPLE 2

A relay optical system according an example 2 will be described below. FIG. 3A is a lens cross-sectional view of the relay optical system according to the example 2. Moreover, FIG. 3B and FIG. 3C are aberration diagrams of the relay optical system according to the example 2, where, FIG. 3B shows a spherical aberration (SA) and FIG. 3C shows an astigmatism (AS).

The relay optical system of the example 2 includes in order from an object side, a first cemented lens CL1 having a positive refractive power, a second cemented lens CL2 having a positive refractive power, a third cemented lens CL3 having a positive refractive power, and a fourth cemented lens CL4 having a positive refractive power. An aperture stop S is disposed between the second cemented lens CL2 and the third cemented lens CL3.

The first cemented lens CL1 includes a biconvex positive lens L1 and a biconcave negative lens L2. The second cemented lens CL2 includes a biconvex positive lens L3 and a negative meniscus lens L4 having a convex surface directed toward an image side. The third cemented lens CL3 includes a negative meniscus lens L5 having a convex surface directed toward the object side and a biconvex positive lens L6. The fourth cemented lens CL4 includes a biconcave negative lens L7 and a biconvex positive lens L8.

In the relay optical system of the example 2, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second cemented lens CL2.

In the relay optical system of the example 2, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 2, a plane of symmetry is at a position of the aperture stop S.

EXAMPLE 3

Figure 4A:
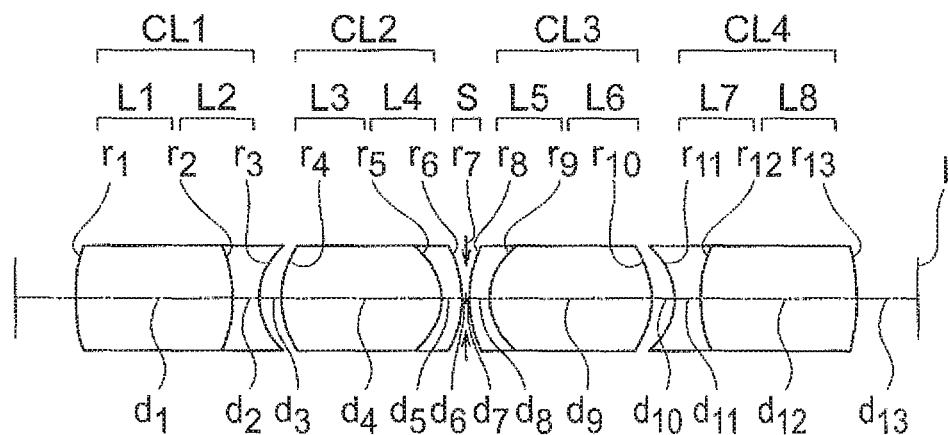
FIG. 4A, and FIG. 4B and FIG. 4C, are a lens cross-sectional view and aberration diagrams respectively, of a relay optical system according to an example 3.
Figure 4B:
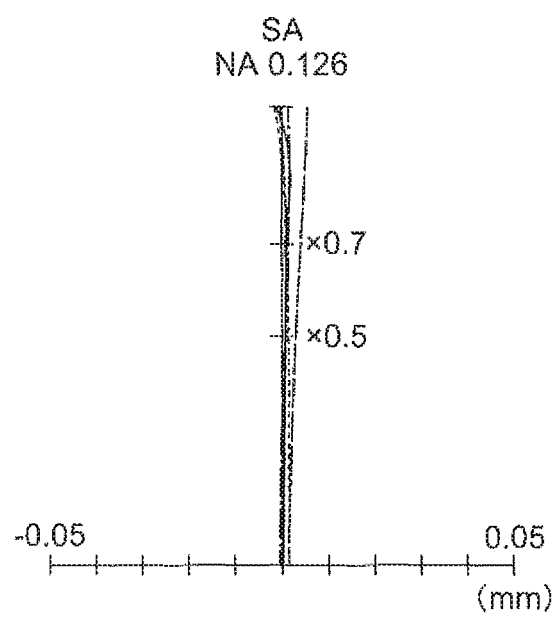
Figure 4C:
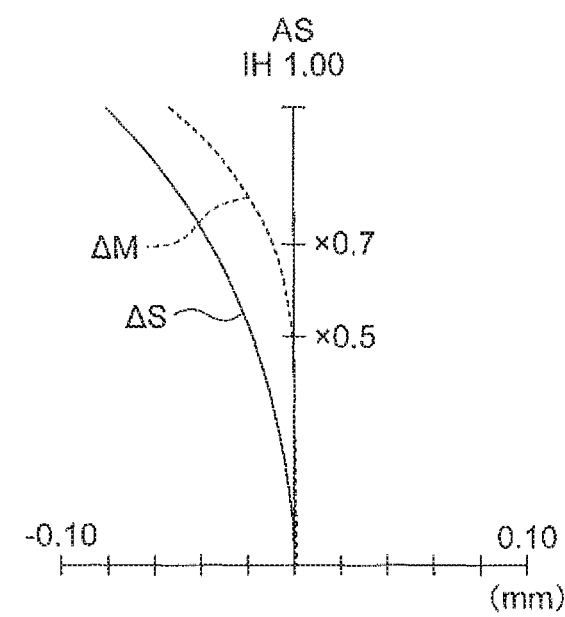

A relay optical system according to an example 3 will be described below. FIG. 4A is a lens cross-sectional view of the relay optical system according to the example 3. Moreover, FIG. 4B and FIG. 4C are aberration diagrams of the relay optical system according to the example 3, where, FIG. 4B shows a spherical aberration (SA) and FIG. 4C shows an astigmatism (AS).

The relay optical system of the example 3 includes in order from an object side, a first cemented lens CL1 having a positive refractive power, a second cemented lens CL2 having a positive refractive power, a third cemented lens CL3 having a positive refractive power, and a fourth cemented lens CL4 having a positive refractive power. An aperture stop S is disposed between the second cemented lens CL2 and the third cemented CL3.

The first cemented lens CL1 includes a biconvex positive lens L1 and a biconcave negative lens L2. The second cemented lens CL2 includes a biconvex positive lens L3 and a negative meniscus lens L4 having a convex surface directed toward an image side. The third cemented lens CL3 includes a negative meniscus lens L5 having a convex surface directed toward the object side and a biconvex positive lens L6. The fourth cemented lens CL4 includes a biconcave negative lens L7 and a biconvex positive lens L8.

In the relay optical system of the example 3, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second cemented lens CL2.

In the relay optical system of the example 3, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 3, a plane of symmetry is at a position of the aperture stop S.

An aspheric surface is provided to a total of two surfaces, which are, an object-side surface of the biconvex positive lens L3 and an image-side surface of the biconvex positive lens L6.

EXAMPLE 4

Figure 5A:
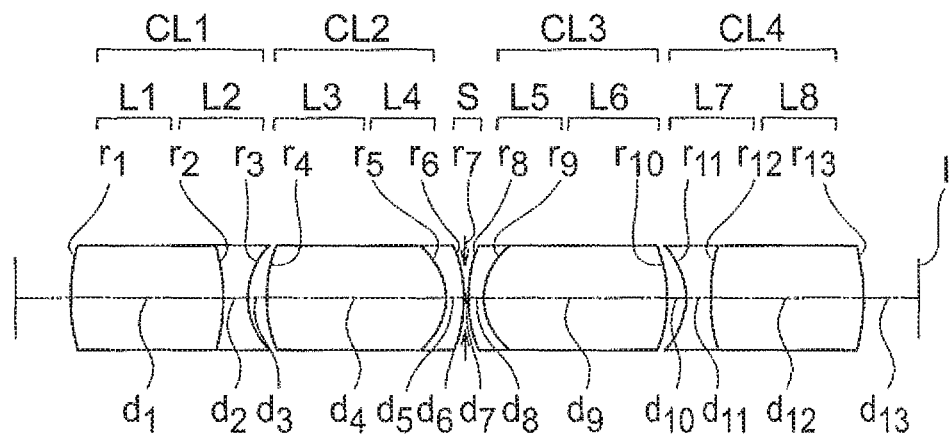
FIG. 5A, and FIG. 5B and FIG. 5C, are a lens cross-sectional view and aberration diagrams respectively, of a relay optical system according to an example 4.
Figure 5B:
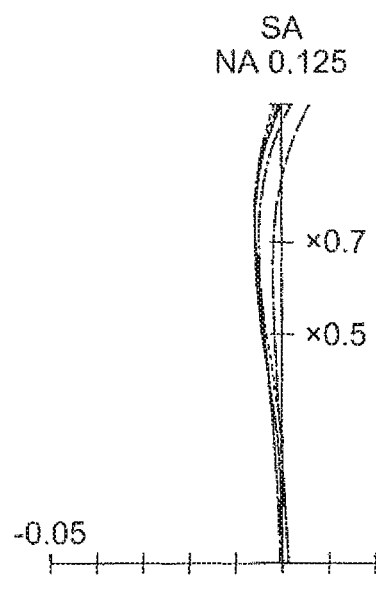
Figure 5C:
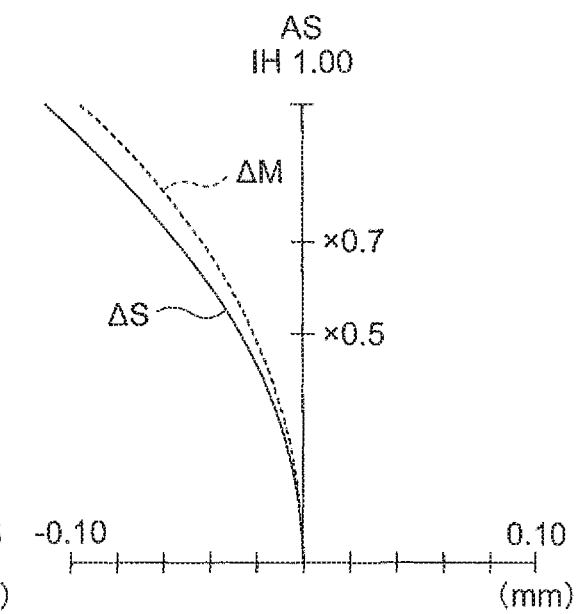

A relay optical system according to an example 4 will be described below. FIG. 5A is a lens cross-sectional view of the relay optical system according to the example 4. Moreover, FIG. 5B and FIG. 5C are aberration diagrams of the relay optical system according to the example 4, where, FIG. 5B shows a spherical aberration (SA) and FIG. 5C shows an astigmatism (AS).

The relay optical system of the example 4 includes in order from an object side, a first cemented lens CL1 having a positive refractive power, a second cemented lens CL2 having a positive refractive power, a third cemented lens CL3 having a positive refractive power, and a fourth cemented lens CL4 having a positive refractive power. An aperture stop S is disposed between the second cemented lens CL2 and the third cemented lens CL3.

The first cemented lens CL1 includes a biconvex positive lens L1 and a biconcave negative lens L2. The second cemented lens CL2 includes a biconvex positive lens L3 and a negative meniscus lens L4 having a convex surface directed toward an image side. The third cemented lens CL3 includes a negative meniscus lens L5 having a convex surface directed toward the object side and a biconvex positive lens L6. The fourth cemented lens CL4 includes a biconcave negative lens L7 and a biconvex positive lens L8.

In the relay optical system of the example 4, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second cemented lens CL2.

In the relay optical system of the example 4, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 4, a plane of symmetry is at a position of the aperture stop S.

EXAMPLE 5

Figure 6A:
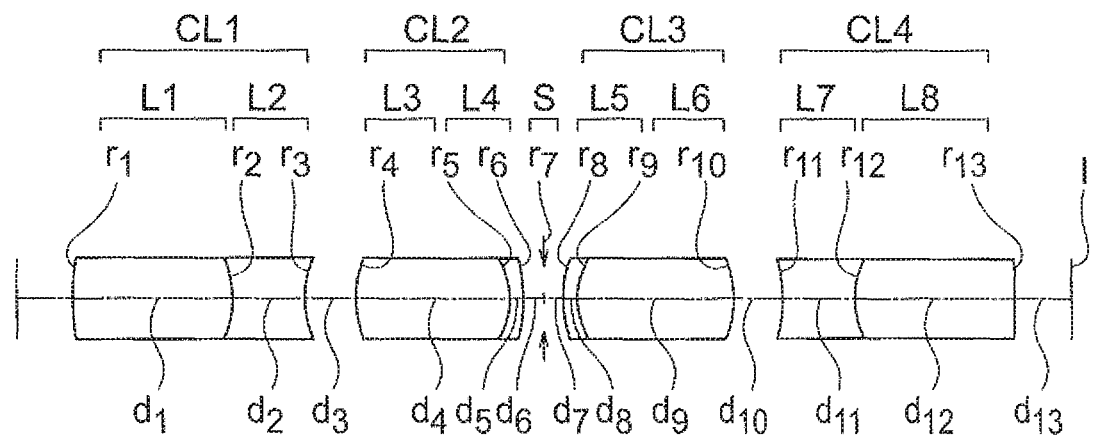
FIG. 6A, and FIG. 6B and FIG. 6C, are a lens cross-sectional view and aberration diagrams respectively, of a relay optical system according to an example 5.
Figure 6B:
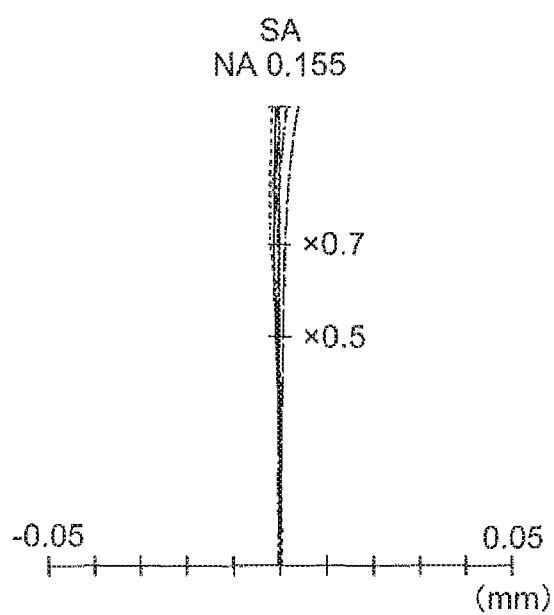
Figure 6C:
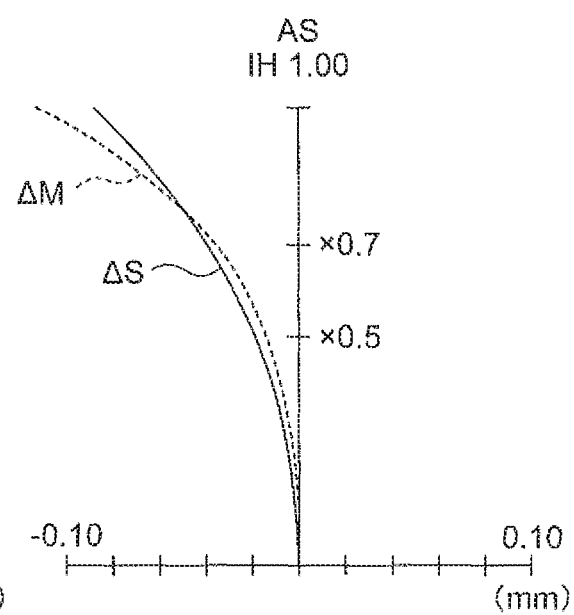

A relay optical system according to an example 5 will be described below. FIG. 6A is a lens cross-sectional view of the relay optical system according to the example 5. Moreover, FIG. 6B and FIG. 6C are aberration diagrams of the relay optical system according to the example 5, where, FIG. 6B shows a spherical aberration (AS) and FIG. 6C shows an astigmatism (AS).

The relay optical system of the example 5 includes in order from an object side, a first cemented lens CL1 having a positive refractive power, a second cemented lens CL2 having a positive refractive power, a third cemented lens CL3 having a positive refractive power, and a fourth cemented lens CL4 having a positive refractive power. An aperture stop S is disposed between the second cemented lens CL2 and the third cemented lens CL3.

The first cemented lens CL1 includes a biconvex positive lens L1 and a biconcave negative lens L2. The second cemented lens CL2 includes a biconvex positive lens L3 and a negative meniscus lens L4 having a convex surface directed toward an image side. The third cemented lens CL3 includes a negative meniscus lens L5 having a convex surface directed toward the object side and a biconvex positive lens L6. The fourth cemented lens CL4 includes a biconcave negative lens L7 and a biconvex positive lens L8.

In the relay optical system of the example 5, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second cemented lens CL2.

In the relay optical system of the example 5, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 5, a plane of symmetry is at a position of the aperture stop S.

An aspheric surface is provided to a total of two surfaces, which are, an object-side surface of the biconvex positive lens L3 and an image-side surface of the biconvex positive lens L6.

EXAMPLE 6

Figure 7A:
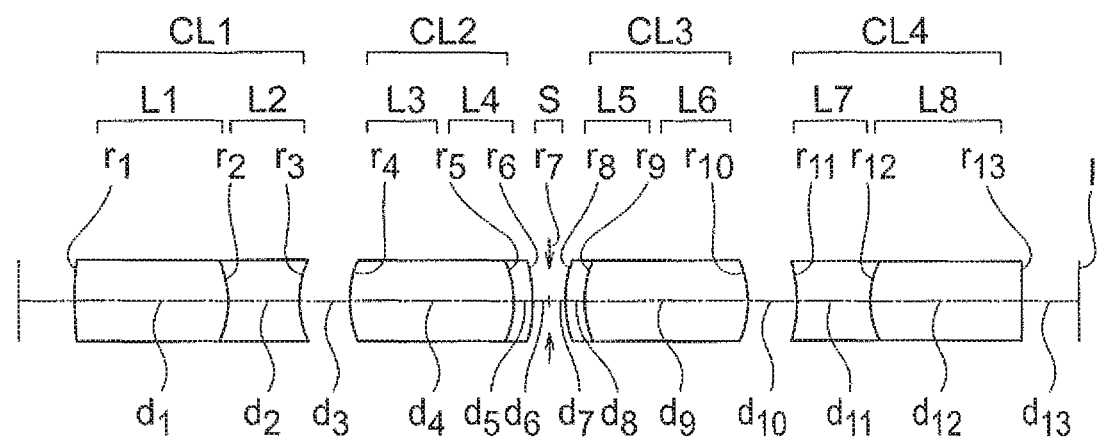
FIG. 7A, and FIG. 7B and FIG. 7C, are a lens cross-sectional view and aberration diagrams respectively, of a relay optical system according to an example 6.
Figure 7B:
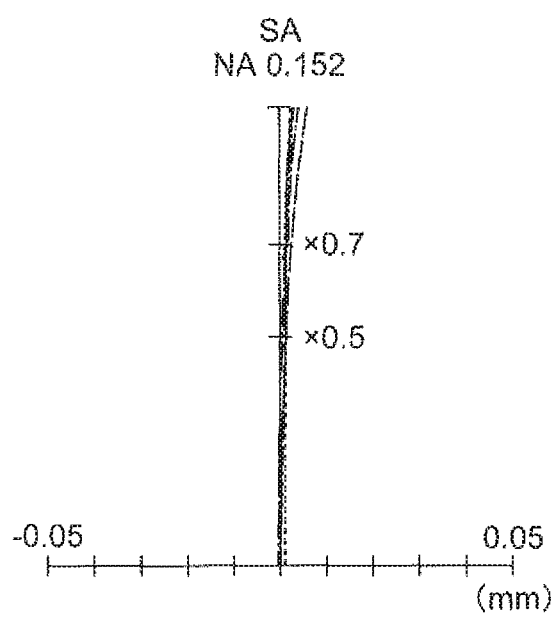
Figure 7C:
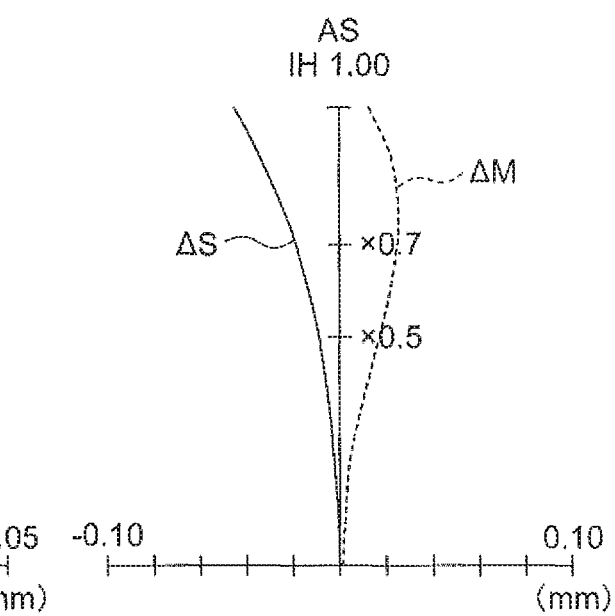

A relay optical system according to an example 6 will be described below. FIG. 7A is a lens cross-sectional view of the relay optical system according to the example 6. Moreover, FIG. 7B and FIG. 7C are aberration diagrams of the relay optical system according to the example 6, where, FIG. 7B shows a spherical aberration (SA) and FIG. 7C shows an astigmatism (AS).

The relay optical system of the example 6 includes in order from an object side, a first cemented lens CL1 having a positive refractive power, a second cemented lens CL2 having a positive refractive power, a third cemented lens CL3 having a positive refractive power, and a fourth cemented lens CL4 having a positive refractive power. An aperture stop S is disposed between the second cemented lens CL2 and the third cemented lens CL3.

The first cemented lens CL1 includes a biconvex positive lens L1 and a biconcave negative lens L2. The second cemented lens CL2 includes a biconvex positive lens L3 and a negative meniscus lens L4 having a convex surface directed toward an image side. The third cemented lens CL3 includes a negative meniscus lens L5 having a convex surface directed toward the object side and a biconvex positive lens L6. The fourth cemented lens CL4 includes a biconcave negative lens L7 and a biconvex positive lens L8.

In the relay optical system of the example 6, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second cemented lens CL2.

In the relay optical system of the example 6, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 6, a plane of symmetry is at a position of the aperture stop S.

An aspheric surface is provided to a total of two surfaces, which are, an object-side surface of the biconvex positive lens L3 and an image-side surface of the biconvex positive lens L6.

EXAMPLE 7

Figure 8A:
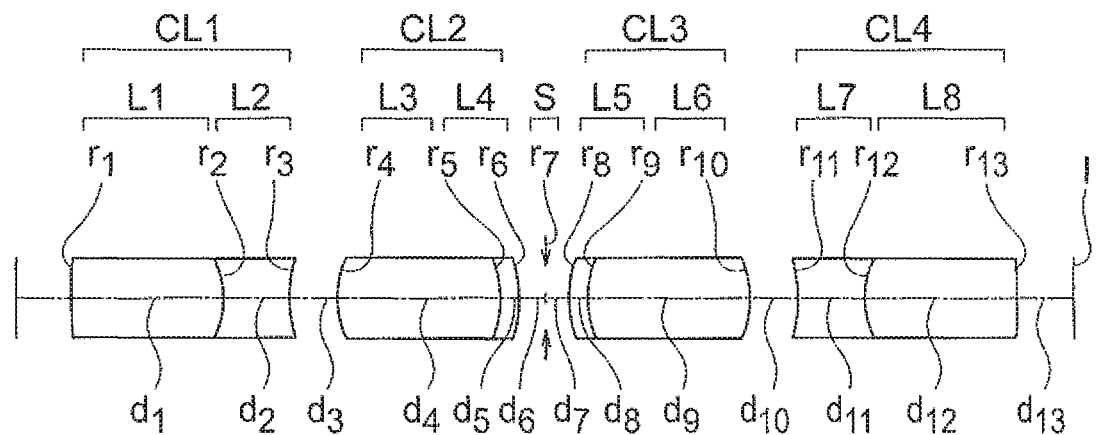
FIG. 8A, and FIG. 8B and FIG. 8C, are a lens cross-sectional view and aberration diagrams respectively, of a relay optical system according to an example 7.
Figure 8B:
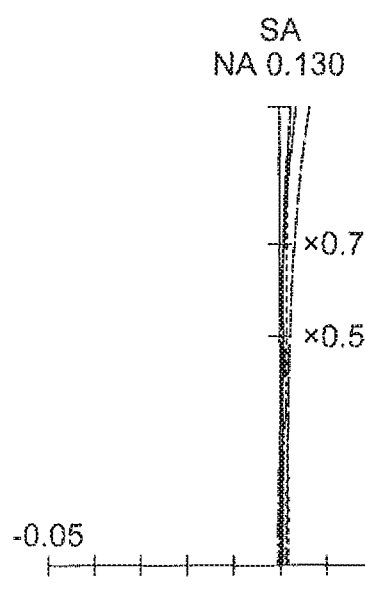
Figure 8C:
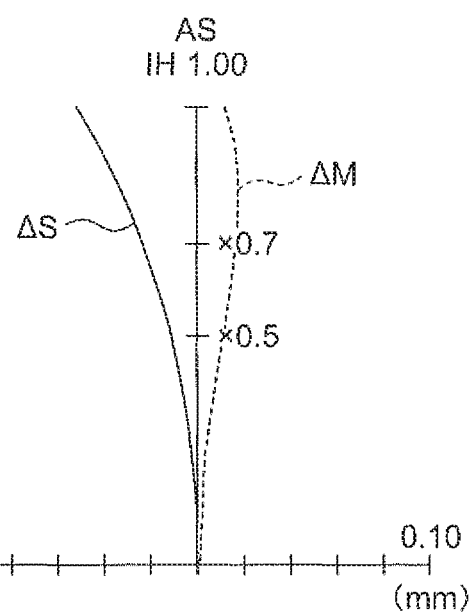

A relay optical system according to an example 7 will be described below. FIG. 8A is a lens cross-sectional view of the relay optical system according to the example 7. Moreover, FIG. 8B and FIG. 8C are aberration diagrams of the relay optical system according to the example 7, where, FIG. 8B shows a spherical aberration (SA) and FIG. 8C shows an astigmatism (AS).

The relay optical system of the example 7 includes in order from an object side, a first cemented lens CL1 having a positive refractive power, a second cemented lens CL2 having a positive refractive power, a third cemented lens CL3 having a positive refractive power, and a fourth cemented lens CL4 having a positive refractive power. An aperture stop S is disposed between the second cemented lens CL2 and the third cemented lens CL3.

The first cemented lens CL1 includes a biconvex positive lens L1 and a biconcave negative lens L2. The second cemented lens CL2 includes a biconvex positive lens L3 and a negative meniscus lens L4 having a convex surface directed toward an image side. The third cemented lens CL3 includes a negative meniscus lens L5 having a convex surface directed toward the object side and a biconvex positive lens L6. The fourth cemented lens CL4 includes a biconcave negative lens L7 and a biconvex positive lens L8.

In the relay optical system of the example 7, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second cemented lens CL2.

In the relay optical system of the example 7, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 7, a plane of symmetry is at a position of the aperture stop S.

An aspheric surface is provided to a total of two surfaces, which are, an object-side surface of the biconvex positive lens L3 and an image-side surface of the biconvex positive lens L6.

EXAMPLE 8

A relay optical system according to an example 8 will be described below. FIG. 9A is a lens cross-sectional view of the relay optical system according to the example 8. Moreover, FIG. 9B and FIG. 9C are aberration diagrams of the relay optical system according to the example 8, where, FIG. 9B shows a spherical aberration (SA) and FIG. 9C shows an astigmatism (AS).

The relay optical system of the example 8 includes in order from an object side, a first cemented lens CL1 having a positive refractive power, a second cemented lens CL2 having a positive refractive power, a third cemented lens CL3 having a positive refractive power, and a fourth cemented lens CL4 having a positive refractive power. An aperture stop S is disposed between the second cemented lens CL2 and the third cemented lens CL3.

The first cemented lens CL1 includes a biconvex positive lens L1 and a biconcave negative lens L2. The second cemented lens CL2 includes a negative meniscus lens L3 having a convex surface directed toward the object side and a biconvex positive lens L4. The third cemented lens CL3 includes a biconvex positive lens L5 and a negative meniscus lens L6 having a convex surface directed toward an image side. The fourth cemented lens CL4 includes a biconcave negative lens L7 and a biconvex positive lens L8.

In the relay optical system of the example 8, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second cemented lens CL2.

In the relay optical system of the example 8, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 8, a plane of symmetry is at a position of the aperture stop S.

An aspheric surface is provided to a total of two surfaces, which are, an object-side surface of the negative meniscus lens L3 and an image-side surface of the negative meniscus lens L6.

EXAMPLE 9

Figure 10A:
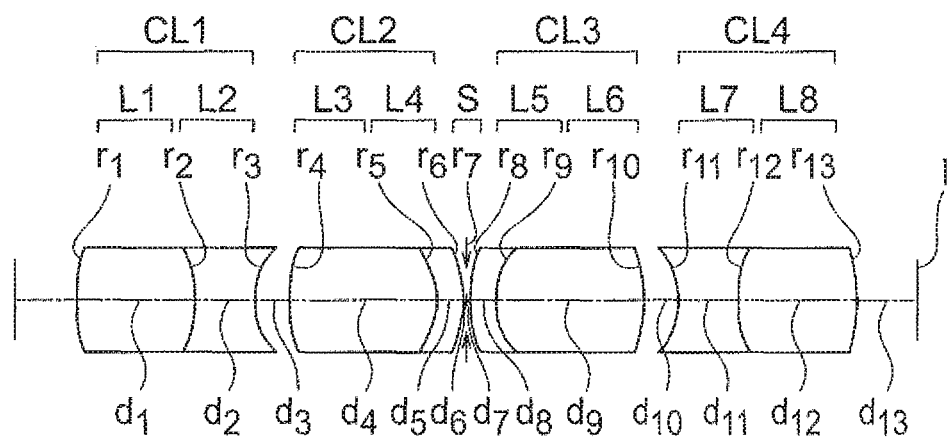
FIG. 10A, and FIG. 10B and FIG. 10C, are a lens cross-sectional view and aberration diagrams respectively, of a relay optical system according to an example 9.
Figure 10B:
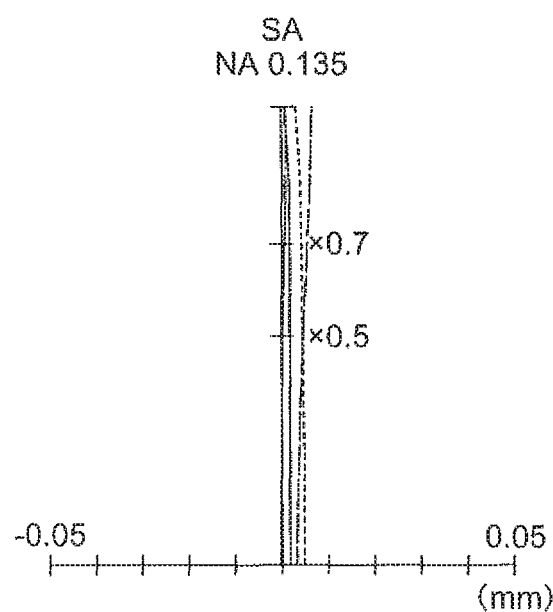
Figure 10C:
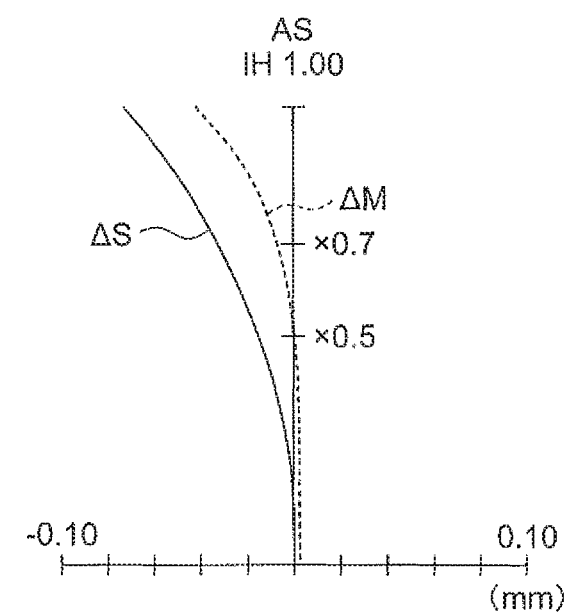

A relay optical system according to an example 9 will be described below. FIG. 10A is a lens cross-sectional view of the relay optical system according to the example 9. Moreover, FIG. 10B and FIG. 10C are aberration diagrams of the relay optical system according to the example 9, where, FIG. 10B shows a spherical aberration (SA) and FIG. 10C shows an astigmatism (AS).

The relay optical system of the example 9 includes in order from an object side, a first cemented lens CL1 having a positive refractive power, a second cemented lens CL2 having a positive refractive power, a third cemented lens CL3 having a positive refractive power, and a fourth cemented lens CL4 having a positive refractive power. An aperture stop S is disposed between the second cemented lens CL2 and the third cemented lens CL3.

The first cemented lens CL1 includes a biconvex positive lens L1 and a biconcave negative lens L2. The second cemented lens CL2 includes a biconvex positive lens L3 and a negative meniscus lens L4 having a convex surface directed toward an image side. The third cemented lens CL3 includes a negative meniscus lens L5 having a convex surface directed toward the object side and a biconvex positive lens L6. The fourth cemented lens CL4 includes a biconcave negative lens L7 and a biconvex positive lens L8.

In the relay optical system of the example 9, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second symmetrical lens CL2.

In the relay optical system of the example 9, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 9, a plane of symmetry is at a position of the aperture stop S.

An aspheric surface is provided to a total of two surfaces, which are, an object-side surface of the biconvex positive lens L3 and an image-side surface of the biconvex positive lens L6.

EXAMPLE 10

A relay optical system according to an example 10 will be described below. FIG. 11A is a lens cross-sectional view of the relay optical system according to the example 10. Moreover, FIG. 11B and FIG. 11C are aberration diagrams of the relay optical system according to the example 10, where, FIG. 11B shows a spherical aberration (SA) and FIG. 11C shows an astigmatism (AS).

The relay optical system of the example 10 includes in order from an object side, a first cemented lens CL1 having a negative refractive power, a second cemented lens CL2 having a positive refractive power, a third cemented lens CL3 having a positive refractive power, and a fourth cemented lens CL4 having a negative refractive power. An aperture stop S is disposed between the second cemented lens CL2 and the third cemented lens CL3.

The first cemented lens CL1 includes a biconvex positive lens L1 and a biconcave negative lens L2. The second cemented lens CL2 includes a biconvex positive lens L3 and a negative meniscus lens L4 having a convex surface directed toward an image side. The third cemented lens CL3 includes a negative meniscus lens L5 having a convex surface directed toward the object side and a biconvex positive lens L6. The fourth cemented lens CL4 includes a biconcave negative lens L7 and a biconvex positive lens L8.

In the relay optical system of the example 10, two sets of cemented lenses are disposed plane-symmetrically. A first set of cemented lenses includes the first cemented lens CL1 and the fourth cemented lens CL4. The fourth cemented lens CL4 has a shape plane-symmetric to a shape of the first cemented lens CL1. The fourth cemented lens CL4 is disposed at a position plane-symmetric to the first cemented lens CL1.

A second set of cemented lenses includes the second cemented lens CL2 and the third cemented lens CL3. The third cemented lens CL3 has a shape plane-symmetric to a shape of the second cemented lens CL2. The third cemented lens CL3 is disposed at a position plane-symmetric to the second symmetrical lens CL2.

In the relay optical system of the example 10, the first cemented lens CL1 and the fourth cemented lens CL4 are symmetric with respect to the aperture stop S. Moreover, the second cemented lens CL2 and the third cemented lens CL3 are symmetric with respect to the aperture stop S. In the relay optical system of the example 10, a plane of symmetry is at a position of the aperture stop S.

An aspheric surface is provided to a total of two surfaces, which are, an object-side surface of the biconvex positive lens L3 and an image-side surface of the biconvex positive lens L6.

Numerical data of each example described above is shown below. In Surface data, in symbols, r denotes radius of curvature of each lens surface, d denotes a distance between respective lens surfaces, ne denotes a refractive index of each lens for a e-line, vd denotes an Abbe number for each lens. Moreover, in various numerical data, NA denotes the numerical aperture, IH denotes the image height, TL denotes the overall length of the relay optical system, θgF3 and θgF4 denote partial dispersion ratio, and PS denotes Petzval sum. The overall length of the relay optical system is a distance between two images (a distance from an object plane up to an image plane in Surface data).

A shape of an aspheric surface is defined by the following expression where the direction of the optical axis is represented by z, the direction orthogonal to the optical axis is represented by y, a conical coefficient is represented by K, aspheric surface coefficients are represented by A4, A6, A8, A10, A12 . . . .

$$Z=(y^2/r)/[1+\{1-(1+k)(y/r)^2\}^{1/2}]+A4y^4+A6y^6+A8y^8+A10y^{10}+A12y^{12}+ \ldots$$

Further, 'E–n' (where, n is an integral number) indicates '$10^{-n}$'. Moreover, these symbols are commonly used in the following numerical data for each example.

EXAMPLE 1

Unit mm

Surface data

| Surface no. | r | d | ne | vd |
|---|---|---|---|---|
| Object plane | ∞ | 1.6920 | | |
| 1 | 4.3492 | 3.4484 | 1.88815 | 40.76 |
| 2 | −2.3878 | 0.9814 | 1.67718 | 38.15 |
| 3 | 1.5712 | 0.6227 | | |
| 4 | 2.8873 | 3.5804 | 1.49846 | 81.54 |
| 5 | −1.6244 | 0.6768 | 1.51825 | 64.14 |
| 6 | −3.3614 | 0.1692 | | |
| 7(Stop) | ∞ | 0.1692 | | |
| 8 | 3.3614 | 0.6768 | 1.51825 | 64.14 |
| 9 | 1.6244 | 3.5804 | 1.49846 | 81.54 |
| 10 | −2.8873 | 0.6227 | | |
| 11 | −1.5712 | 0.9814 | 1.66718 | 38.15 |
| 12 | 2.3878 | 3.4484 | 1.88815 | 40.76 |
| 13 | −4.3492 | 1.6920 | | |
| Image plane | ∞ | | | |

Various data

| NA | 0.1000 |
|---|---|
| IH | 1.000 |
| TL | 22.34 |
| θgF3 | 0.5375 |
| θgF4 | 0.5353 |
| PS | 0.1810 |

EXAMPLE 2

Unit mm

Surface data

| Surface no. | r | d | ne | vd |
|---|---|---|---|---|
| Object plane | ∞ | 1.6920 | | |
| 1 | 4.3492 | 3.4484 | 1.88815 | 40.76 |
| 2 | −2.3878 | 0.9814 | 1.67718 | 38.15 |
| 3 | 1.5712 | 0.6227 | | |
| 4 | 2.8873 | 3.5804 | 1.49846 | 81.54 |
| 5 | −1.6244 | 0.6768 | 1.51825 | 64.14 |
| 6 | −3.3614 | 0.1692 | | |
| 7(Stop) | ∞ | 0.1692 | | |
| 8 | 3.3614 | 0.6768 | 1.51825 | 64.14 |
| 9 | 1.6244 | 3.5804 | 1.49846 | 81.54 |
| 10 | −2.8873 | 0.6227 | | |
| 11 | −1.5712 | 0.9814 | 1.66718 | 38.15 |
| 12 | 2.3878 | 3.4484 | 1.88815 | 40.76 |
| 13 | −4.3492 | 1.6920 | | |
| Image plane | ∞ | | | |

Various data

| NA | 0.0794 |
|---|---|
| IH | 1.000 |
| TL | 22.34 |
| θgF3 | 0.5375 |
| θgF4 | 0.5353 |
| PS | 0.1810 |

EXAMPLE 3

Unit mm

Surface data

| Surface no. | r | d | ne | vd |
|---|---|---|---|---|
| Object plane | ∞ | 1.4989 | | |
| 1 | 5.5468 | 3.9128 | 2.01169 | 28.27 |
| 2 | −3.4156 | 0.6815 | 1.62409 | 36.26 |
| 3 | 1.7079 | 0.5501 | | |
| 4* | 2.6173 | 4.0384 | 1.43985 | 94.93 |
| 5 | −1.6017 | 0.5039 | 1.51825 | 64.14 |
| 6 | −2.9709 | 0.1004 | | |
| 7(Stop) | ∞ | 0.1004 | | |
| 8 | 2.9709 | 0.5039 | 1.51825 | 64.14 |
| 9 | 1.6017 | 4.0384 | 1.43985 | 94.93 |
| 10* | −2.6173 | 0.5501 | | |

-continued

Unit mm

| | | | | |
|---|---|---|---|---|
| 11 | −1.7079 | 0.6815 | 1.62409 | 36.26 |
| 12 | 3.4156 | 3.9128 | 2.01169 | 28.27 |
| 13 | −5.5468 | 1.4989 | | |
| Image plane | ∞ | | | |

Aspherical surface data

4th surface

K = 1.3352
A4 = −7.8861E−03

10th surface

K = 1.3352
A4 = 7.8861E−03

Various data

| | |
|---|---|
| NA | 0.126 |
| IH | 1.000 |
| TL | 22.57 |
| θgF3 | 0.534 |
| θgF4 | 0.5353 |
| PS | 0.2193 |

EXAMPLE 4

Unit mm

Surface data

| Surface no. | r | d | ne | vd |
|---|---|---|---|---|
| Object plane | ∞ | 1.3469 | | |
| 1 | 5.5824 | 3.8133 | 2.01169 | 28.27 |
| 2 | −4.3058 | 0.6304 | 1.62409 | 36.26 |
| 3 | 2.0846 | 0.4326 | | |
| 4 | 3.3001 | 4.5940 | 1.43985 | 94.93 |
| 5 | −1.6484 | 0.3877 | 1.51825 | 64.14 |
| 6 | −2.8785 | 0.0852 | | |
| 7(Stop) | ∞ | 0.0852 | | |
| 8 | 2.8785 | 0.3877 | 1.51825 | 64.14 |
| 9 | 1.6484 | 4.5940 | 1.43985 | 94.93 |
| 10 | −3.3001 | 0.4326 | | |
| 11 | −2.0846 | 0.6304 | 1.62409 | 36.26 |
| 12 | 4.3058 | 3.8133 | 2.01169 | 28.27 |
| 13 | −5.5824 | 1.3469 | | |
| Image plane | ∞ | | | |

Various data

| | |
|---|---|
| NA | 0.1246 |
| IH | 1.000 |
| TL | 22.58 |
| θgF3 | 0.534 |
| θgF4 | 0.5353 |
| PS | 0.2454 |

EXAMPLE 5

Unit mm

Surface data

| Surface no. | r | d | ne | vd |
|---|---|---|---|---|
| Object plane | ∞ | 1.8167 | | |
| 1 | 19.5954 | 5.0378 | 2.01169 | 28.27 |
| 2 | −3.2960 | 2.2706 | 1.62409 | 36.26 |
| 3 | 3.9954 | 1.5727 | | |
| 4* | 3.6196 | 4.8760 | 1.43985 | 94.93 |
| 5 | −2.6864 | 0.4529 | 1.69979 | 55.53 |
| 6 | −5.0412 | 0.6291 | | |
| 7(Stop) | ∞ | 0.6291 | | |
| 8 | 5.0412 | 0.4529 | 1.69979 | 55.53 |
| 9 | 2.6864 | 4.8760 | 1.43985 | 94.93 |
| 10* | −3.6196 | 1.5727 | | |
| 11 | −3.9954 | 2.2706 | 1.62409 | 36.26 |
| 12 | 3.2960 | 5.0378 | 2.01169 | 28.27 |
| 13 | −19.5954 | 1.8167 | | |
| Image plane | ∞ | | | |

Aspherical surface data

4th surface

K = 0.0343
A4 = −2.8223E−03

10th surface

K = 0.0343
A4 = 2.8223E−03

Various data

| | |
|---|---|
| NA | 0.1546 |
| IH | 1.000 |
| TL | 33.31 |
| θgF3 | 0.534 |
| θgF4 | 0.5434 |
| PS | 0.1840 |

EXAMPLE 6

Unit mm

Surface data

| Surface no. | r | d | ne | vd |
|---|---|---|---|---|
| Object plane | ∞ | 1.7935 | | |
| 1 | 19.9317 | 4.8199 | 2.01169 | 28.27 |
| 2 | −3.3856 | 2.2765 | 1.62409 | 36.26 |
| 3 | 4.0449 | 1.5636 | | |
| 4* | 3.5769 | 5.1751 | 1.43985 | 94.93 |
| 5 | −2.7738 | 0.5759 | 1.69979 | 55.53 |
| 6 | −5.1694 | 0.5347 | | |
| 7(Stop) | ∞ | 0.5347 | | |
| 8 | 5.1694 | 0.5759 | 1.69979 | 55.53 |
| 9 | 2.7738 | 5.1751 | 1.43985 | 94.93 |
| 10* | −3.5769 | 1.5636 | | |
| 11 | −4.0449 | 2.2765 | 1.62409 | 36.26 |
| 12 | 3.3856 | 4.8199 | 2.01169 | 28.27 |
| 13 | −19.9317 | 1.7935 | | |
| Image plane | ∞ | | | |

-continued

Unit mm

Aspherical surface data

4th surface

K = 0.0323
A4 = −3.4447E−03

10th surface

K = 0.0323
A4 = 3.4447E−03

Various data

| | |
|---|---|
| NA | 0.1524 |
| IH | 1.000 |
| TL | 33.48 |
| θgF3 | 0.534 |
| θgF4 | 0.5434 |
| PS | 0.1841 |

EXAMPLE 7

Unit mm

Surface data

| Surface no. | r | d | ne | vd |
|---|---|---|---|---|
| Object plane | ∞ | 1.7893 | | |
| 1 | 15.3350 | 4.7990 | 2.01169 | 28.27 |
| 2 | −3.8708 | 2.1366 | 1.62409 | 36.26 |
| 3 | 4.0920 | 1.5293 | | |
| 4* | 3.9257 | 5.0818 | 1.43985 | 94.93 |
| 5 | −2.6180 | 0.5884 | 1.65425 | 58.55 |
| 6 | −4.8779 | 0.7316 | | |
| 7(Stop) | ∞ | 0.7316 | | |
| 8 | 4.8779 | 0.5884 | 1.65425 | 58.55 |
| 9 | 2.6180 | 5.0818 | 1.43985 | 94.93 |
| 10* | −3.9257 | 1.5293 | | |
| 11 | −4.0920 | 2.1366 | 1.62409 | 36.26 |
| 12 | 3.8708 | 4.7990 | 2.01169 | 28.27 |
| 13 | −15.3350 | 1.7893 | | |
| Image plane | ∞ | | | |

Aspherical surface data

4th surface

K = 0.5062
A4 = −3.3438E−03

10th surface

K = 0.5062
A4 = 3.3438E−03

Various data

| | |
|---|---|
| NA | 0.13 |
| IH | 1.000 |
| TL | 33.31 |
| θgF3 | 0.534 |
| θgF4 | 0.5424 |
| PS | 0.1881 |

EXAMPLE 8

Unit mm

Surface data

| Surface no. | r | d | ne | vd |
|---|---|---|---|---|
| Object plane | ∞ | 1.6672 | | |
| 1 | 3.8459 | 3.3078 | 1.88815 | 40.76 |
| 2 | −6.4323 | 1.1905 | 1.72538 | 34.71 |
| 3 | 1.7657 | 0.6553 | | |
| 4* | 3.5464 | 0.9993 | 1.51825 | 64.06 |
| 5 | 1.5741 | 3.1690 | 1.49846 | 81.54 |
| 6 | −3.0729 | 0.0948 | | |
| 7(Stop) | ∞ | 0.0948 | | |
| 8 | 3.0729 | 3.1690 | 1.49846 | 81.54 |
| 9 | −1.5741 | 0.9993 | 1.51825 | 64.06 |
| 10* | −3.5464 | 0.6553 | | |
| 11 | −1.7657 | 1.1905 | 1.72538 | 34.71 |
| 12 | 6.4323 | 3.3078 | 1.88815 | 40.76 |
| 13 | −3.8459 | 1.6672 | | |
| Image plane | ∞ | | | |

Aspherical surface data

4th surface

K = 2.1601
A4 = −1.2021E−02

10th surface

K = 2.1601
A4 = 1.2021E−02

Various data

| | |
|---|---|
| NA | 0.125 |
| IH | 1.000 |
| TL | 22.17 |
| θgF3 | 0.5333 |
| θgF4 | 0.5375 |
| PS | 0.1819 |

EXAMPLE 9

Unit mm

Surface data

| Surface no. | r | d | ne | vd |
|---|---|---|---|---|
| Object plane | ∞ | 1.5203 | | |
| 1 | 5.0823 | 2.9710 | 1.88815 | 40.76 |
| 2 | −3.2361 | 1.4800 | 1.61669 | 44.27 |
| 3 | 1.9643 | 0.8708 | | |
| 4* | 3.7520 | 3.7050 | 1.49846 | 81.54 |
| 5 | −2.0323 | 0.6446 | 1.61669 | 44.27 |
| 6 | −3.4301 | 0.0941 | | |
| 7(Stop) | ∞ | 0.0941 | | |
| 8 | 3.4301 | 0.6446 | 1.61669 | 44.27 |
| 9 | 2.0323 | 3.7050 | 1.49846 | 81.54 |
| 10* | −3.7520 | 0.8708 | | |
| 11 | −1.9643 | 1.4800 | 1.61669 | 44.27 |
| 12 | 3.2361 | 2.9710 | 1.88815 | 40.76 |
| 13 | −5.0823 | 1.5203 | | |
| Image plane | ∞ | | | |

-continued

Unit mm

Aspherical surface data

4th surface
K = 0.7292
A4 = −4.0535E−03
10th surface
K = 0.7292
A4 = 4.0535E−03

Various data

| | |
|---|---|
| NA | 0.125 |
| IH | 1.000 |
| TL | 22.57 |
| θgF3 | 0.5375 |
| θgF4 | 0.5633 |
| PS | 0.2034 |

EXAMPLE 10

Unit mm

Surface data

| Surface no. | r | d | ne | vd |
|---|---|---|---|---|
| Object plane | ∞ | 1.7096 | | |
| 1 | 24.7277 | 4.5913 | 2.01169 | 28.27 |
| 2 | −2.5922 | 1.1081 | 1.62409 | 36.26 |
| 3 | 2.7376 | 1.5000 | | |
| 4* | 2.8362 | 6.5368 | 1.43985 | 94.93 |
| 5 | −2.3436 | 0.5671 | 1.69979 | 55.53 |
| 6 | −4.6762 | 0.8560 | | |
| 7(Stop) | ∞ | 0.8560 | | |
| 8 | 4.6762 | 0.5671 | 1.69979 | 55.53 |
| 9 | 2.3436 | 6.5368 | 1.43985 | 94.93 |
| 10* | −2.8362 | 1.5000 | | |
| 11 | −2.7376 | 1.1081 | 1.62409 | 36.26 |
| 12 | 2.5922 | 4.5913 | 2.01169 | 28.27 |
| 13 | −24.7277 | 1.7095 | | |
| Image plane | ∞ | | | |

Aspherical surface data

4th surface

K = −0.3449
A4 = −2.4423E−03

10th surface

K = −0.3449
A4 = 2.4423E−03

Various data

| | |
|---|---|
| NA | 0.140 |
| IH | 1.000 |
| TL | 33.74 |
| θgF3 | 0.534 |
| θgF4 | 0.5434 |
| PS | 0.1523 |

Next, the values of conditional expressions in each example are shown below.
Conditional Expression $$f2/fCL12 \quad (1)$$

$$PS \times TL \quad (2)$$

$$|(fCL2/fCL1) \times (\theta gF3 - \theta gF4)/(vd3 - vd4)| \quad (3)$$

$$f2/fCL2 \quad (4)$$

$$f1/fCL12 \quad (5)$$

Conditional expression

| | Example1 | Example2 | Example3 |
|---|---|---|---|
| (1) | −0.178 | −0.178 | −0.258 |
| (2) | 4.043 | 4.043 | 4.949 |
| (3) | 2.833E−05 | 2.833E−05 | 1.102E−05 |
| (4) | −0.311 | −0.311 | −0.393 |
| (5) | 0.321 | 0.321 | 0.398 |

| | Example4 | Example5 | Example6 |
|---|---|---|---|
| (1) | −0.318 | −0.321 | −0.324 |
| (2) | 5.541 | 6.130 | 6.162 |
| (3) | 1.48E−05 | 8.6E−05 | 8.096E−05 |
| (4) | −0.444 | −0.372 | −0.378 |
| (5) | 0.437 | 0.390 | 0.392 |

| | Example7 | Example8 | Example9 |
|---|---|---|---|
| (1) | −0.343 | −0.232 | −0.248 |
| (2) | 6.266 | 4.032 | 4.591 |
| (3) | 8.538E−05 | 7.267E−05 | 25.2E−05 |
| (4) | −0.406 | −0.423 | −0.372 |
| (5) | 0.415 | 0.411 | 0.372 |

| | Example10 |
|---|---|
| (1) | −0.246 |
| (2) | 5.139 |
| (3) | 4.105E−06 |
| (4) | −0.317 |
| (5) | 0.316 |

Various embodiments of the present invention have been described heretofore. However, the present invention is not restricted to these embodiments described above, and embodiments in which arrangements of these embodiments are combined appropriately without departing from the scope of the present invention are also in the category of the present invention.

According to the present embodiments, it is possible to provide a relay optical system in which a curvature of field, a spherical aberration, and a chromatic aberration have been corrected favorably, and a rigid endoscope having the relay optical system.

The present invention is useful for a relay optical system in which the curvature of field, the spherical aberration, and the chromatic aberration are corrected favorably, and a rigid endoscope using the relay optical system.

What is claimed is:

1. A relay optical system comprising, in order from an object side:
   a first cemented lens;
   a second cemented lens having a positive refractive power;
   a third cemented lens which is plane-symmetric to the second cemented lens; and
   a fourth cemented lens which is plane-symmetric to the first cemented lens,
   wherein:
   the first cemented lens includes a first lens having a positive refractive power and a second lens having a negative refractive power, the second cemented lens includes a third lens and a fourth lens, a shape of the first lens is a biconvex shape, a shape of the second lens is a biconcave shape, and the following conditional expression (1) is satisfied:

$$-0.4 < f2/fCL12 < -0.1 \qquad (1)$$

where, f2 denotes a focal length of the second lens, and fCL12 denotes a combined focal length of the first cemented lens and the second cemented lens.

2. The relay optical system according to claim 1, wherein the third lens has a positive refractive power and the fourth lens has a negative refractive power.

3. The relay optical system according to claim 1, wherein the third lens has a negative refractive power and the fourth lens has a positive refractive power.

4. The relay optical system according to claim 1, wherein a lens surface on an object side of the third lens is an aspheric surface.

5. The relay optical system according to claim 1, wherein the following conditional expression (2) is satisfied:

$$3 < PS \times TL < 8 \qquad (2)$$

where,

PS denotes Petzval sum, and

TL denotes an overall length of the relay optical system.

6. The relay optical system according to claim 1, wherein the following conditional expression (3) is satisfied:

$$0.5E-5 < |(fCL2/fCL1) \times (\theta gF3 - \theta gF4)/(vd3 - vd4)| < 100E-5 \qquad (3)$$

where, fCL1 denotes a focal length of the first cemented lens, fCL2 denotes a focal length of the second cemented lens, θgF3 denotes a partial dispersion ratio for the third lens, θgF4 denotes a partial dispersion ratio for the fourth lens, vd3 denotes Abbe's number for the third lens, and vd4 denotes Abbe's number for the fourth lens.

7. The relay optical system according to claim 1, wherein the following conditional expression (4) is satisfied:

$$-0.5 < f2/fCL2 < -0.2 \qquad (4)$$

where, fCL2 denotes a focal length of the second cemented lens.

8. A rigid endoscope comprising the relay optical system according to claim 1.

* * * * *